United States Patent
Schmidt

(10) Patent No.: US 8,206,341 B2
(45) Date of Patent: Jun. 26, 2012

(54) DEVICE AND PROCESS FOR CONTROLLING THE DEPTH OF SEDATION OF A MECHANICALLY RESPIRATED PATIENT

(75) Inventor: Hartmut Schmidt, Heilshoop (DE)

(73) Assignee: Dräger Medical GmbH, Lübeck (DE)

( * ) Notice: Subject to any disclaimer, the term of this patent is extended or adjusted under 35 U.S.C. 154(b) by 234 days.

(21) Appl. No.: 12/265,147

(22) Filed: Nov. 5, 2008

(65) Prior Publication Data

US 2009/0177181 A1    Jul. 9, 2009

(30) Foreign Application Priority Data

Jan. 4, 2008  (DE) .......................... 10 2008 003 237

(51) Int. Cl.
*A61M 31/00* (2006.01)
(52) U.S. Cl. .......................... 604/67; 604/503
(58) Field of Classification Search .................... 604/65, 604/66, 67, 503; 128/204.18; 600/554
See application file for complete search history.

(56) References Cited

U.S. PATENT DOCUMENTS

| 6,745,764 B2 * | 6/2004 | Hickle ..................... 128/203.12 |
| 2007/0010756 A1 * | 1/2007 | Viertio-Oja ................... 600/544 |

FOREIGN PATENT DOCUMENTS

| DE | 100 15 026 C2 | 10/2001 |
| DE | 602004008673 T2 | 6/2008 |
| EP | 11 77 764 B1 | 2/2002 |

* cited by examiner

*Primary Examiner* — Kevin C Sirmons
*Assistant Examiner* — Brandy C Scott
(74) *Attorney, Agent, or Firm* — McGlew and Tuttle, P.C.

(57) ABSTRACT

A device is provided for controlling the depth of sedation of a respirated patient. The device includes a respirator (2) and a sensor array (1) for detecting the tidal volume and/or the respiration rate of the patient being respirated. A computing unit (5) is provided for calculating the measured values determined with the sensor array (1). A drug regulating unit (3), a drug dispensing unit (4), and a central control device (6) are provided. The central control device (6) has stored desired values for the drug concentration to be dispensed as a function of a preselected depth of sedation corresponding to the corresponding variability over time of the tidal volume and/or respiration rate. The drug regulating unit (3) sets the drug dispensing unit (4) as a function of the tidal volume detected and/or the respiration rate for a preselected depth of sedation of the patient.

17 Claims, 1 Drawing Sheet

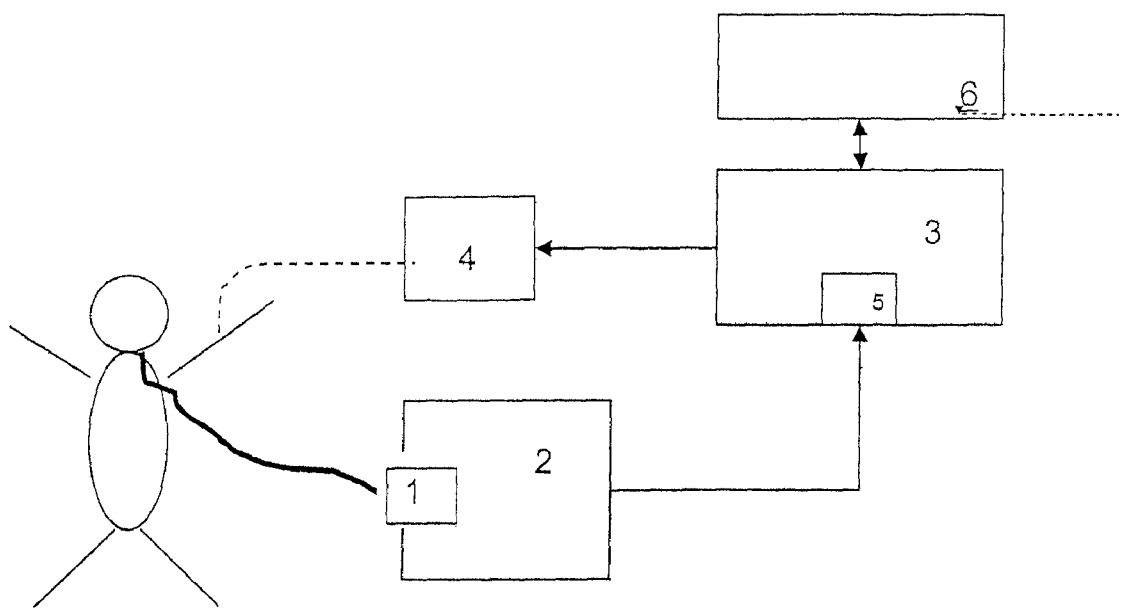

DEVICE AND PROCESS FOR CONTROLLING THE DEPTH OF SEDATION OF A MECHANICALLY RESPIRATED PATIENT

CROSS REFERENCE TO RELATED APPLICATIONS

This application claims the benefit of priority under 35 U.S.C.§119 of German Patent Application DE 10 2008 003 237.9 filed Jan. 4, 2008, the entire contents of which are incorporated herein by reference.

FIELD OF THE INVENTION

The present invention pertains to a device and a process for controlling the depth of sedation of a patient respirated mechanically by means of a respirator in intensive care, i.e., usually in intensive care areas or units in hospitals.

BACKGROUND OF THE INVENTION

A device and a process for regulating a numerical value for respirating a patient with a higher-level control circuit appears from DE 100 15 026 C2, where an anesthetic is dispensed in a mixture of gaseous anesthetics.

Mechanically respirated patients in intensive care also receive narcotics, i.e., sedatives, besides analgesic drugs. The sedatives are used to tranquilize mechanically respirated patients.

It is difficult to control the depth of sedation because patients sedated too deeply recover more slowly. On the other hand, weaning from the mechanical respiration requires a lower depth of sedation. New medical therapy guidelines recommend a daily interruption of or pause in sedation with a subsequent extubation test.

In addition, the sedatives consumed represent a considerable cost factor in intensive care.

SUMMARY OF THE INVENTION

Consequently, it is desirable and therefore the object of the present invention to provide an improved device and a process by means of which device and process it is possible to measure and control the depth of sedation.

According to the invention, a device is provided for controlling the depth of sedation of a mechanically respirated (also known as ventilated) patient. The device comprises a respirator and a sensor array for detecting the tidal volume and/or a respiration rate of the patient being respirated with a respirator (also known as ventilator). A computing unit is provided for calculating the measured values detected with the sensor array. A drug regulating unit is provided along with a drug dispensing unit for dispensing a drug to the patient being respirated. A central control device is provided with stored desired values for the drug concentration to be dispensed as a function of a preselected depth of sedation corresponding to the corresponding variability over time of the tidal volume and/or the respiration rate. The drug regulating unit sets the drug dispensing unit as a function of the detected tidal volume and/or the respiration rate for a preselected depth of sedation of the patient.

The measured values determined in the computing unit may be calculated into parameters for the variability over time of the respiration rate and/or the tidal volume. Classification or assessment rules for depths of sedation as a function of the measured variability over time of the respiration rate and/or tidal volume may be stored in the central control device. The classification or assessment rules may be based on scoring methods. The classification or assessment rules based on scoring methods may comprise one of Ramsay Sedation Scale (RSS), Sedation Agitation Scale (SAS), Motor Activity Assessment Scale (MAAS), Vancouver Interaction and Calmness Scale (VICS), Richmond Agitation Sedation Score (RASS), and Cook-Palma Scale.

Therapy data corresponding to individual therapy protocols are additionally stored in the central control device with defined, prioritized depths of sedation for preset points in time.

The sensor array may be arranged in the respiration system of the respirator. The computing unit and the drug regulating unit may advantageously comprise a single assembly unit.

The drug dispensing unit may advantageously comprise a microfluid pump or a piezoelectric dispensing unit.

According to another aspect of the invention, a process is provided for controlling the depth of sedation of a mechanically respirated patient. The process comprises the steps of inducing sedation using a preset drug dispensing, so that the desired depth of sedation corresponds to the actual depth of sedation. A control circuit is closed by switching on a drug regulating unit, so that a time-dependent tidal volume flow and/or the respiration rate of the patient is measured. Parameters for the variability over time of the tidal volume and/or the respiration rate are calculated from the measured values and corresponding depths of sedation are determined by means of classification or assessment rules. The drug dispensing is set for a preset desired depth of sedation based on stored rules for the relationship between the depth of sedation and the drug concentration to be dispensed.

The device according to the present invention and the process according to the present invention are based on the observation that the variability, i.e., the changeability depends on the depth of sedation of the patient corresponding to the variation over time of the respiration rate and/or the tidal volume. A deeply sedated patient shows no variability in his or her breathing pattern, whereas an awake patient has a great variability in his or her breathing pattern.

Since sedation is carried out especially in case of mechanically respirated patients, the patient's breathing pattern can be determined directly from the tidal volume flow measurement, which is integrated, in general, in the respirator, and the tidal volume derived therefrom by integration over time. The variability over time of the respiration rate and/or breath volume, i.e., tidal volume, is obtained from the breathing pattern determined. The dispensing of drugs, especially of sedatives, in a dispensing unit, especially in an infusion pump, is adapted by means of a control device.

Moreover, the depth of sedation can be varied over the course of the day by means of a time profile stored optionally in the control device with a device according to the present invention. For example, the automatic awakening of a patient at a predetermined point in time is thus possible, so that an automatic extubation test can likewise be carried out automatically by means of a signal sent especially from the control device, for example, before a visit by the physician.

In addition, it is possible to pass on quality parameters to a higher-level patient data processing system or to a higher-level treatment platform by means of the device indicated, so that the progression of the treatment can be documented, on the one hand, and improvements in quality can be implemented in the current treatment, on the other hand.

An exemplary embodiment of the present invention will be explained below on the basis of the only figure, which schematically shows the arrangement of a device for controlling the depth of sedation of a mechanically respirated patient.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

The only FIGURE is a schematic view showing features of the device and process according to the invention.

DESCRIPTION OF THE PREFERRED EMBODIMENTS

Referring to the drawing in particular, the device shown for regulating the depth of sedation has a respirator 2, which is known per se, and a sensor array 1 for measuring the tidal volume flow of a patient and for determining his tidal volume. A drug regulating unit 3 is used to set a drug dispensing unit 4, especially an infusion pump, for the drug concentration currently being dispensed, including one or more sedatives. A computing unit 5 of the drug regulating unit 3 calculates the variability over time of the tidal volume. Another, central control device 6, which may also be designed as one assembly unit with the drug regulating unit 3, is used to control the depth of sedation of the patient being respirated.

The tidal volume flow of the patient is measured by means of the sensor array 1 and the tidal volume is determined from the measured value by integration over time. The computing unit 5 calculates from this tidal volume the variability of the tidal volume over a predetermined period of time and makes this measured value available to the drug regulating unit 3 as an actual value for the current depth of sedation.

Depending on the therapy data being stored in the central control device 6 and correspondingly associated therapy protocols, the desired depth of sedation of the patient is preset for the drug regulating unit 3 corresponding to a corresponding drug concentration to be administered. The particular depths of sedation are stored in the central control device 6 corresponding to the classification or assessment methods used in the particular hospital.

Such scoring methods are, for example, Ramsay Sedation Scale (RSS), Sedation Agitation Scale (SAS), Motor Activity Assessment Scale (MAAS), Vancouver Interaction and Calmness Scale (VICS), Richmond Agitation Sedation Score (RASS), and Cook-Palma Scale.

The central control device 6 converts these rules into a corresponding tidal volume variability. For example, the tidal volume variability is below 150 for a Cook-Palma value of <5 corresponding to oversedation. A sedation of 2 to 3 according to the Ramsay Sedation Scale (RSS) is typically desirable for patients requiring intensive care. The central control device 6 transmits the desired drug delivery rate to the drug regulating unit 3. For the drug propofol, which is frequently used as a sedative at 2% concentration, the drug delivery rate ranges from 3.0 mL to 14 mL per hour at a typical concentration of 20 mg/mL and an allowable maximum dose of 4.5 mg per kg of body weight per hour for an adult of average age with a body weight of 70 kg.

The drug regulating unit 3 has a PID controller and regulates the release of drug by the drug dispensing unit 4 to the patient. If the variability of the tidal volume drops to below 150 but only moderate depth of sedation is desired, the drug regulating unit 3 reduces the quantity of drug released until the desired depth of sedation is reached. For example, the rate of delivery of the drug dispensing unit 4 is now reduced, for example, from 10 mL per hour to 5 mL per hour for the sedative propofol in a 2% solution. The drug regulating unit 3 correspondingly increases the quantity of drug released if the variability of the tidal volume is too high. However, the rate of drug delivery of the drug dispensing unit 4 is increased only up to the maximum allowable, preset rate of delivery, which is complied with during the regulation. The dose is limited to a maximum of 4.5 mg per kg of body weight and per hour in case of propofol in a 2% solution.

Each patient responds differently to changes in the depth of sedation with a variability of the tidal volume. When the sedation is being induced, the central control device 6 at first controls the drug dispensing according to the physician's instructions, without using the drug regulating unit 3, until the actual depth of sedation corresponds to the desired depth of sedation. The central control device 6 can automatically calibrate the conversion curve between the preset depth of sedation and the variability of the tidal volume. When the desired depth of sedation is reached, the control circuit with the drug regulating unit 3 is closed and the delivery rate of the drug dispensing unit 4 is regulated as described above.

The term "respirator" (also the term ventilator) also includes anesthesia apparatuses.

While specific embodiments of the invention have been shown and described in detail to illustrate the application of the principles of the invention, it will be understood that the invention may be embodied otherwise without departing from such principles.

What is claimed is:

1. A device for controlling the depth of sedation of a mechanically respirated patient, the device comprising:
   a respirator;
   a sensor array detecting a tidal volume and/or a respiration rate of the patient being respirated with said respirator;
   a computing unit calculating measured values detected with the sensor array;
   a drug regulating unit;
   a drug dispensing unit for dispensing a drug to the patient being respirated; and
   a central control device with stored desired values for a drug concentration to be dispensed as a function of a preselected depth of sedation corresponding to a corresponding variability over time of the tidal volume and/or the respiration rate, wherein the drug regulating unit sets the drug dispensing unit as a function of the detected tidal volume and/or the respiration rate for a preselected depth of sedation of the patient, wherein the measured values determined in the computing unit are calculated into parameters for the variability over time of the respiration rate and/or the tidal volume.

2. A device in accordance with claim 1, wherein classification or assessment rules for depths of sedation as a function of the measured variability over time of the respiration rate and/or tidal volume are stored in the central control device.

3. A device in accordance with claim 2, wherein the classification or assessment rules are based on scoring methods.

4. A device in accordance with claim 3, wherein the classification or assessment rules based on scoring methods comprise one of Ramsay Sedation Scale (RSS), Sedation Agitation Scale (SAS), Motor Activity Assessment Scale (MAAS), Vancouver Interaction and Calmness Scale (VICS), Richmond Agitation Sedation Score (RASS), and Cook-Palma Scale.

5. A device in accordance with claim 1, wherein therapy data corresponding to individual therapy protocols are additionally stored in the central control device with defined, prioritized depths of sedation for preset points in time.

6. A device in accordance with claim 1, wherein said sensor array is arranged in the respiration system of the respirator.

7. A device in accordance with claim 1, wherein said computing unit and said drug regulating unit comprise a single assembly unit.

8. A device in accordance with claim 1, wherein said drug dispensing unit is an infusion pump, said infusion pump dispensing said drug to the patient intravenously.

9. A process of controlling the depth of sedation of a mechanically respirated patient, the process comprising the steps of:
  providing a respirator and respirating a patient with said respirator;
  providing a sensor array for detecting the tidal volume and/or a respiration rate of the patient being respirated with said respirator;
  providing a computing unit;
  calculating measured values detected with said sensor array using said computing unit;
  providing a drug regulating unit;
  providing a drug dispensing unit;
  providing a central control device with stored desired values for a drug concentration to be dispensed as a function of a preselected depth of sedation corresponding to a corresponding variability over time of the tidal volume and/or the respiration rate;
  dispensing a drug with the drug dispensing unit to the patient being respirated for inducing sedation using a preset drug dispensing rate having a desired depth of sedation corresponding to the actual depth of sedation;
  switching on the drug regulating unit, so that a time-dependent tidal volume flow and/or the respiration rate of the patient is measured;
  calculating parameters that represent the variability over time of the tidal volume and/or the respiration rate from the measured values and determining corresponding depths of sedation by means of classification or assessment rules using the central control device; and
  setting drug dispensing for a preset desired depth of sedation based on stored rules for the relationship between the depth of sedation and the drug concentration to be dispensed wherein the drug regulating unit sets the drug dispensing unit as a function of the parameters that represent the variability of the detected tidal volume and/or the respiration rate for the preselected depth of sedation of the patient.

10. A process in accordance with claim 9, wherein classification or assessment rules for depths of sedation as a function of the measured variability over time of the respiration rate and/or tidal volume are stored in the central control device, the classification or assessment rules are based on scoring methods comprise one of Ramsay Sedation Scale (RSS), Sedation Agitation Scale (SAS), Motor Activity Assessment Scale (MAAS), Vancouver Interaction and Calmness Scale (VICS), Richmond Agitation Sedation Score (RASS), and Cook-Palma Scale.

11. A device in accordance with claim 1, wherein said drug regulating increases said drug concentration with an increase in said variability over time of said tidal volume.

12. A process of controlling a depth of sedation of a patient, the process comprising the steps of:
  predetermining a desired depth of sedation for the patient;
  determining an initial drug dosage to place the patient at the desired depth of sedation;
  administering the initial drug dosage to the patient;
  measuring respiration of the patient over time after said administration of the initial drug dose;
  calculating a respiration variability parameter representing how the respiration varies over time from said measuring step;
  equating the respiration variability parameter with an actual depth of sedation;
  comparing said desired depth of sedation with said actual depth of sedation;
  selectively administering future drug dosages to the patient to minimize a difference between the desired depth of sedation and the actual depth of sedation.

13. A process in accordance with claim 12, wherein:
  said measuring includes measuring one of a tidal volume and a respiration rate;
  said respiration variability parameter is a variability of said one of the respiration rate and the tidal volume.

14. A process in accordance with claim 12, further comprising:
  mechanically respirating the patient.

15. A process in accordance with claim 12, wherein:
  said determining of the desired variability is performed by administering a sufficient amount of the drug to bring the patient to the desired depth of sedation according to a predetermined scoring method, measuring the variability of the tidal volume or respiration rate at the desired depth of sedation, and using the measured variability at the desired depth of sedation according to the predetermined scoring method as the desired variability.

16. A process in accordance with claim 12, further comprising:
  changing the desired depth of sedation over time;
  determining the desired variability of tidal volume or respiration rate corresponding to the changes in desired depth of sedation;
  selectively administering the future drug dosages to the patient to minimize a difference between the desired variability at a present time and the actual variability.

17. A process in accordance with claim 12, wherein:
  said selectively administering of the drug increases the drug dosage with an increase in the actual variability.

* * * * *